United States Patent
Xia et al.

(10) Patent No.: US 9,176,506 B2
(45) Date of Patent: Nov. 3, 2015

(54) LOW PRESSURE AND HIGH-LOW TEMPERATURE TEST BOX CAPABLE OF CONTROLLING HUMIDITY

(75) Inventors: Keyu Xia, Guangdong (CN); Jiaming Zhang, Guangdong (CN)

(73) Assignee: DONGGUAN CITY SIMPLEWELL TECHNOLOGY CO., LTD., Guangdong (CN)

( * ) Notice: Subject to any disclaimer, the term of this patent is extended or adjusted under 35 U.S.C. 154(b) by 341 days.

(21) Appl. No.: 13/878,755

(22) PCT Filed: Oct. 18, 2010

(86) PCT No.: PCT/CN2010/077813
§ 371 (c)(1),
(2), (4) Date: Apr. 11, 2013

(87) PCT Pub. No.: WO2012/051746
PCT Pub. Date: Apr. 26, 2012

(65) Prior Publication Data
US 2013/0193219 A1    Aug. 1, 2013

(51) Int. Cl.
G05D 22/02 (2006.01)
B01L 1/00 (2006.01)
G01M 99/00 (2011.01)
G01N 17/00 (2006.01)
G05D 16/14 (2006.01)

(52) U.S. Cl.
CPC . G05D 22/02 (2013.01); B01L 1/00 (2013.01); G01M 99/002 (2013.01); G01N 17/002 (2013.01); G05D 16/14 (2013.01); *B01L 2200/142* (2013.01)

(58) Field of Classification Search
CPC ...... G05D 16/14; G05D 22/02; G01M 99/002; G01N 17/002; B01L 1/00; B01L 2200/142
USPC ........................................................ 236/44 C
See application file for complete search history.

(56) References Cited

U.S. PATENT DOCUMENTS

| 4,142,403 A * | 3/1979 | Lohnes et al. ..................... 73/76 |
| 4,822,117 A * | 4/1989 | Boston, Jr. .................. 312/257.1 |
| 5,318,361 A | 6/1994 | Chase et al. |
| 6,272,767 B1 * | 8/2001 | Botruff et al. ................... 34/202 |

FOREIGN PATENT DOCUMENTS

| CN | 201035028 Y | 3/2008 |
| CN | 201149588 Y | 11/2008 |
| CN | 101554941 A * | 10/2009 |
| CN | 101614724 A | 12/2009 |
| CN | 201357073 Y | 12/2009 |

(Continued)

Primary Examiner — Marc Norman

(57) ABSTRACT

A low pressure and high-low temperature test box capable of controlling humidity comprises a test box body (1), a first heater (2) and a first evaporator (3) which are installed in the test box body (1), a humiture sensor (4) for detecting the humiture inside the test box body (1) and a vacuum manometer (5) for detecting the pressure inside the test box body (1) which are both installed on the test box body (1), an air circulation device (6) for circulating the air inside the test box body (1), and a humidity adjusting device (7) which is connected to the test box body (1) and used for adjusting the humidity inside the test box body (1). A vacuum pump (8) for vacuumizing the test box body (1) is also provided on the test box body (1).

8 Claims, 3 Drawing Sheets

(56) References Cited

FOREIGN PATENT DOCUMENTS

| | | |
|---|---|---|
| CN | 201419101 Y | 3/2010 |
| CN | 101832619 A | 9/2010 |
| CN | 101858876 A | 10/2010 |
| JP | 1-116464 A | 5/1989 |
| JP | 2-72647 A | 3/1990 |
| JP | 11-51823 A | 2/1999 |
| JP | 2008-89564 A | 4/2008 |
| WO | WO 02/33391 A1 | 4/2002 |

* cited by examiner

LOW PRESSURE AND HIGH-LOW TEMPERATURE TEST BOX CAPABLE OF CONTROLLING HUMIDITY

BACKGROUND OF THE INVENTION

The present invention relates to a low pressure and high-low temperature test device, specifically to a low pressure and high-low temperature test box capable of controlling humidity that can automatically control humidity and temperature of the test environment according to the needs of the test environment.

A test box currently used for the low pressure and high-low temperature test of materials or devices is used for detecting the properties of materials or devices at a certain temperature under the low pressure condition, that is, this test box is used only for detecting the temperature and pressure instead of humidity therein; however, humidity is also an important factor affecting properties of materials or devices, because humidity may also affect properties of materials or devices. Therefore, the conventional test box used for the low pressure and high-low temperature test of materials or devices cannot be used for detecting properties of material or devices. Thus a test environment meeting the requirements needs to be provided, so as to improve the detection accuracy.

BRIEF SUMMARY OF THE INVENTION

For overcoming the above disadvantages of the prior art, a purpose of the present invention is to provide a low pressure and high-low temperature test box capable of controlling humidity that can simultaneously detect and control temperature/humidity and pressure in the test box, which can effectively meet the needs of the test environment and improve the detection accuracy.

In order to attain the above purpose, the present invention provides the following technical solution: A low pressure and high-low temperature test box capable of controlling humidity is constructed, comprising a test box body, a first heater and a first evaporator installed inside the test box body, a temperature-humidity sensor installed on the test box body used for detecting the temperature/humidity therein, and a vacuum manometer used for detecting the pressure inside the test box body; the low pressure and high-low temperature test box capable of controlling humidity further comprises an air circulation device used for circulating the air inside the test box body, and a humidity regulating device connected to inside the test box body for regulating the humidity thereof; the test box body is further provided with a vacuum pump used for vacuuming the inside thereof.

The humidity regulating device further includes a dry air intake device, which includes a second capillary connected to the dry air intake pipe, and a second control valve, the second control valve being connected at its air outtake pipe to an air outtake pipe of the water-gas control valve.

The air outtake pipe of the first capillary and the second capillary is connected to a proportional regulating valve, whose air outtake pipe is connected to inside the test box body.

The water tank is further provided inside with a second heater and a second evaporator.

The low pressure and high-low temperature test box capable of controlling humidity of the present invention has the following beneficial effects: A test box body is constructed, provided inside with a first heater and a first evaporator; the test box body is provided with a temperature-humidity sensor used for detecting the temperature/humidity therein, a vacuum manometer used for detecting the pressure therein, also an air circulation device used for circulating the air therein, and a humidity regulating device connected to inside the test box body for regulating the humidity thereof; the test box body is further provided with a vacuum pump used for vacuuming the inside thereof. With regulation of the humidity inside the test box through the humidity regulating device, the influence of humidity on the properties of materials or devices can be valuated and detected; this test box can simultaneously detect and control temperature/humidity and pressure therein, effectively meeting the needs of the test environment and improving the detection accuracy.

The low pressure and high-low temperature test box capable of controlling humidity of the present invention will further be described below with reference to drawings and examples:

DETAILED DESCRIPTION OF THE INVENTION

The most preferred examples of the low pressure and high-low temperature test box capable of controlling humidity of the present invention as shown in the following cannot thereby limit the extent of protection of the present invention.

Figure 1:
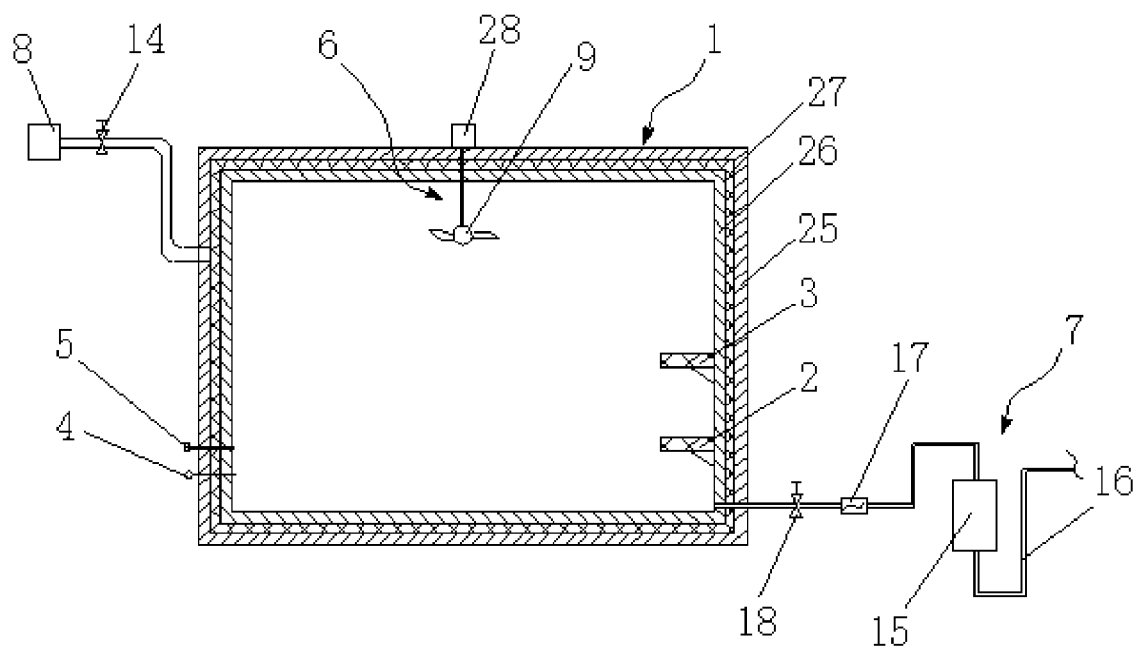
FIG. 1 is a structural schematic drawing of the low pressure and high-low temperature test box capable of controlling humidity of the present invention.
Figure 2:
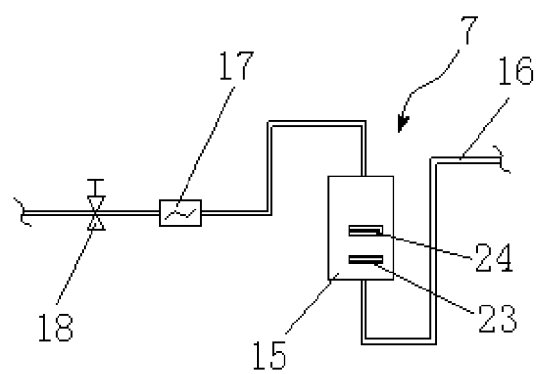
FIG. 2 is a first structural schematic drawing of the humidity regulating device of the low pressure and high-low temperature test box capable of controlling humidity of the present invention.

As shown in FIGS. 1 and 2, a low pressure and high-low temperature test box capable of controlling humidity is provided, comprising: a test box body 1, a first heater 2 and a first evaporator 3 installed inside the test box body 1, a temperature-humidity sensor 4 installed on the test box body 1 for detecting the temperature/humidity therein, and a vacuum manometer 5 used for detecting the pressure inside the test box body 1; the low pressure and high-low temperature test box capable of controlling humidity further comprises an air circulation device 6 used for circulating the air inside the test box body 1, and a humidity regulating device 7 connected to inside the test box body 1 for regulating the humidity thereof; the test box body 1 is further provided with a vacuum pump 8 for vacuuming therein.

The vacuum pump 8 is controlled through a first control valve 14 installed on a pipeline connecting the test box body 1 to the vacuum pump 8 as well as through a frequency converter; a drive motor 28 is connected to a stirring fan 9 through a magnetic coupling, which ensures that the test box is sealed, the stirring fan 9 stirring the air inside the test box body 1 to make the air therein mixed uniformly.

The vacuum pump 8 is controlled through a first control valve 14 installed on a pipeline connecting the test box body 1 to the vacuum pump 8 as well as through a frequency converter, with the vacuum pressure controlled by regulating rotational speed of the vacuum pump 8.

The humidity regulating device 7 is composed of a water tank 15, an air intake pipe 16 connected to a lower air intake pipe of the water tank 15, and a water-gas control valve 18 connected to an upper air outtake pipe of the water tank 15, the water tank 15 containing water inside for humidifying the air; the air intake pipe 16 is further provided with a first capillary or a first throttle device 17 used for regulating air input or water inflow, which is installed in front of or at the rear of the water-gas control valve 18; the water tank 15 is further provided inside with a second heater 23 and a second evaporator 24, which are used for regulating temperature of the water inside the water tank 15 and controlling the water content of the air going through the water tank; and the water tank 15 is further provided inside with a temperature sensor, which is used for controlling and detecting the water temperature and making the water temperature constant.

The test box body 1 is composed of an outer housing 25, an inner liner 26, and an insulating layer 27 between the outer housing 25 and the inner liner 26; the test box is a low-pressure device, with its box body needing to withstand the pressure; the inner liner 26, as a thickened plate, withstands the pressure, or the outer housing 25 improves the capability of withstanding the pressure.

Figure 3:
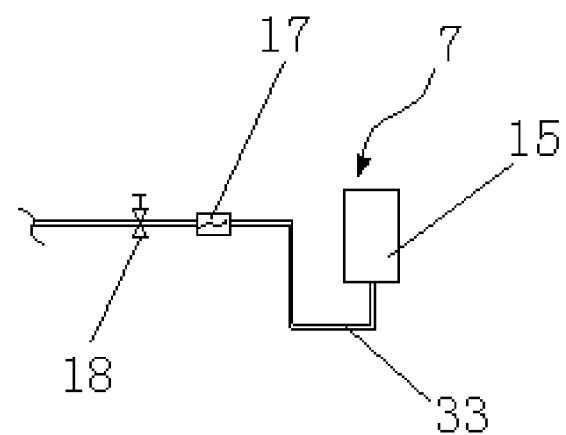
FIG. 3 is a second structural schematic drawing of the humidity regulating device of the low pressure and high-low temperature test box capable of controlling humidity of the present invention.

As shown in FIG. 3, the humidity regulating device 7 is composed of a water tank 15, a water intake pipe 33 connected to the lower air intake pipe of the water tank 15, and a water-gas control valve 18 installed on the water intake pipe 33, the water tank 15 containing water inside; the water intake pipe 33 is further provided with a first capillary or a first throttle device 17 used for regulating air input or water inflow that, installed in front of or at the rear of the water-gas control valve 18, directly inhales into the test box body 1 by means of the internal vacuum of the test box, with natural evaporation increasing the internal humidity of the test box body 1.

Figure 4:
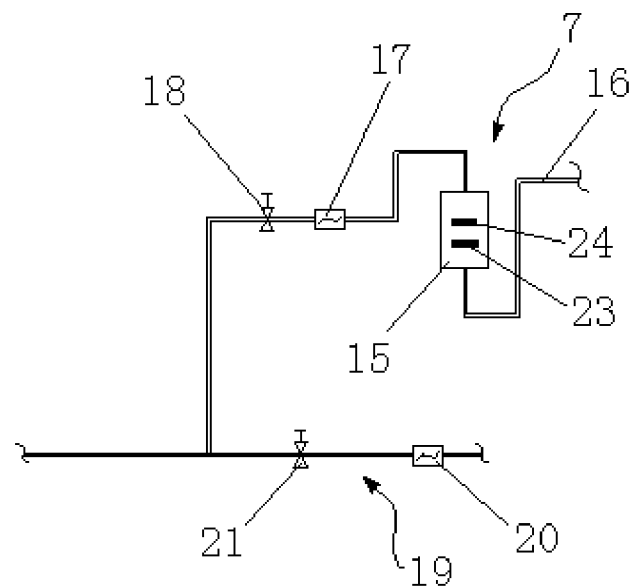
FIG. 4 is a third structural schematic drawing of the humidity regulating device of the low pressure and high-low temperature test box capable of controlling humidity of the present invention.

As shown in FIG. 4, the humidity regulating device 7 further includes a dry air intake device 19, which includes a second capillary and a second throttle device 20 connected to the dry air intake pipe, and a second control valve 21, the second control valve 21 being connected at its air outtake pipe to an air outtake pipe of the water-gas control valve 18, the second capillary or the second throttle device 20 being installed in front of or at the rear of the second control valve 21.

Figure 5:
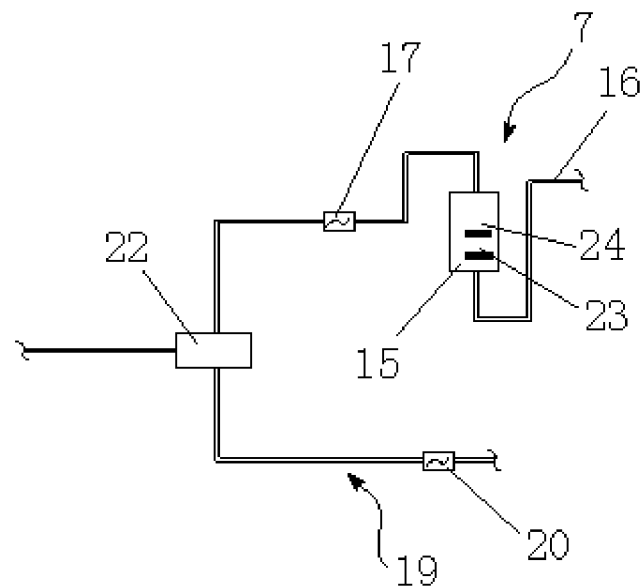
FIG. 5 is a fourth structural schematic drawing of the humidity regulating device of the low pressure and high-low temperature test box capable of controlling humidity of the present invention.

As shown in FIG. 5, an outtake pipe of the first capillary or first throttle device 17 and the second capillary or second throttle device 20 is connected to a proportional regulating valve 22, whose outtake pipe is connected to inside the test box body 1, with the humidity inside the test box body 1 being regulated by the proportional regulating valve 22 after the dry and wet airs are mixed in proportion.

Figure 6:
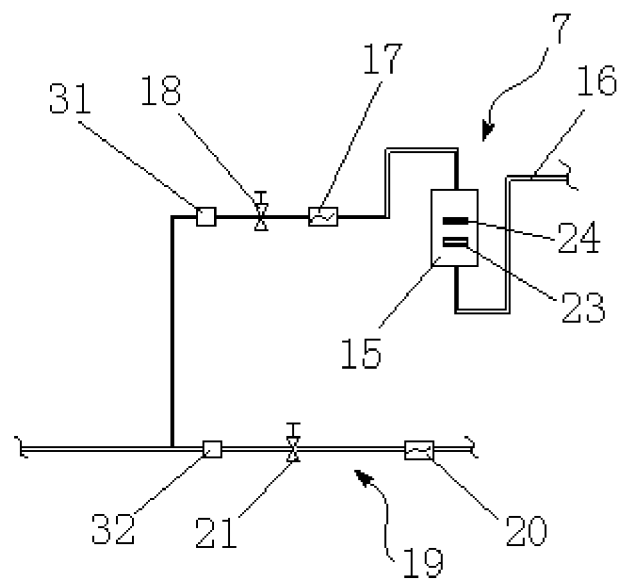
FIG. 6 is a fifth structural schematic drawing of the humidity regulating device of the low pressure and high-low temperature test box capable of controlling humidity of the present invention.

As shown in FIG. 6, the dry air intake device 19 is further provided on its pipeline with a first air flow automatic control device 32, and the air intake pipe 16 is further provided with a second air flow automatic control device 31; a test box controller, according to the internal humidity of the test box body 1, automatically regulates the flow ratio of one of the two loops entering into the test box, with the flow of air or water in the other loop capable of being fixed.

The above solution ensures that the internal humidity of the test box is controllable under low pressure and low temperature conditions. The test box can also be provided inside with a humidifying water tray or outside with a pressure-withstanding humidifier; with this humidifying method, the humidifying capacity of the humidifier is high, and the humidity of the test box in the low pressure and non-low temperature state can be controlled by controlling heat productivity of the humidifier.

The above examples are preferred embodiments of the present invention. However, the embodiments of the present invention are free from restriction of the above examples; and any other modification, amendment, replacement, combination and simplification not departing from the spirit and principle of the present invention shall be the equivalent substitution, and all fall within the extent of protection of the present invention.

What is claimed is:

1. A low pressure and high-low temperature test box capable of controlling humidity,
comprising: a test box body (1), a first heater (2) and a first evaporator (3) installed inside the test box body (1), a temperature and humidity sensor (4) installed on the test box body (1) used for detecting temperature and humidity therein, and a vacuum manometer (5) used for detecting pressure inside the test box body (1); characterized in that the test box further comprises an air circulation device (6) used for circulating air inside the test box body (1), and a humidity regulating device (7) connected to inside the test box body (1) for regulating the humidity thereof, the test box body (1) being further provided with a vacuum pump (8) used for vacuuming the inside thereof; the humidity regulating device (7) is composed of a water tank (15), an air intake pipe (16) connected to a lower air intake pipe of the water tank (15), and a water-gas control valve (18) connected to an upper air outtake pipe of the water tank (15), the water tank (15) containing water inside.

2. The low pressure and high-low temperature test box capable of controlling humidity according to claim 1, characterized in that the vacuum pump (8) is controlled through a first control valve (14) installed on a pipeline connecting the test box body (1) to the vacuum pump (8) as well as through a frequency converter.

3. The low pressure and high-low temperature test box capable of controlling humidity according to claim 1 characterized in that the air intake pipe (16) is further provided with a first capillary or a first throttle device (17) used for regulating air input, which is installed in front of or at rear side of the water-gas control valve (18).

4. The low pressure and high-low temperature test box capable of controlling humidity according to claim 3, characterized in that the humidity regulating device (7) further includes a dry air intake device (19), which includes a second capillary or a second throttle device (20) connected to a dry air intake pipe as well as a second control valve (21), the second control valve (21) being connected at its air outtake pipe to an air outtake pipe of the water-gas control valve (18), the second capillary or the second throttle device (20) being installed in front of or at a rear side of the second control valve (21).

5. The low pressure and high-low temperature test box capable of controlling humidity according to claim 4, characterized in that the dry air intake device (19) is further provided on its pipeline with a first air flow automatic control device (32), and the air intake pipe (16) is further provided with a second air flow automatic control device (31).

6. The low pressure and high-low temperature test box capable of controlling humidity according to claim 4, characterized in that an outtake pipe of the first capillary or first throttle device (17) and the second capillary or second throttle device (20) are connected to a proportional regulating valve (22), whose air outtake pipe is connected to inside the test box body (1).

7. The low pressure and high-low temperature test box capable of controlling humidity according to claim 6, characterized in that the water tank (15) is further provided inside with a second heater (23) and a first evaporator (24), and the water tank (15) is further provided inside with a temperature sensor.

8. The low pressure and high-low temperature test box capable of controlling humidity according to claim 1, characterized in that the test box body (1) is composed of an outer housing (25), an inner liner (26), and an insulating layer (27) between the outer housing (25) and the inner liner (26).

* * * * *